(12) United States Patent
Ebisawa et al.

(10) Patent No.: US 8,338,174 B2
(45) Date of Patent: Dec. 25, 2012

(54) MATERIAL FOR AMELIORATING SKIN TISSUE AND METHOD FOR PRODUCING THE SAME

(75) Inventors: Katsumi Ebisawa, Nagoya (JP); Ryuji Kato, Nagoya (JP); Hideaki Kagami, Nagoya (JP); Minoru Ueda, Nagoya (JP)

(73) Assignee: National University Corporation Nagoya University, Aichi (JP)

( * ) Notice: Subject to any disclaimer, the term of this patent is extended or adjusted under 35 U.S.C. 154(b) by 524 days.

(21) Appl. No.: 12/490,764

(22) Filed: Jun. 24, 2009

(65) Prior Publication Data

US 2010/0260722 A1 Oct. 14, 2010

(30) Foreign Application Priority Data

Dec. 28, 2006 (JP) ................................ 2006-354259

(51) Int. Cl.
*C12N 5/07* (2010.01)
(52) U.S. Cl. ......... 435/371; 435/373; 435/378; 435/383
(58) Field of Classification Search .................. 435/325, 435/371, 373, 378
See application file for complete search history.

(56) References Cited

U.S. PATENT DOCUMENTS

| 5,591,444 | A | 1/1997 | Boss, Jr. |
| 6,284,262 | B1 * | 9/2001 | Place ........................... 424/435 |

FOREIGN PATENT DOCUMENTS

| JP | 11-510069 | 9/1999 |
| WO | 97/04720 | 2/1997 |
| WO | 2007/001016 | 1/2007 |

OTHER PUBLICATIONS

Chinnathambi et al., The Anatomical Record, Part A, 270A:162-174, 2003.*
Buurma, et al. Transplantation of human pulpal and gingival fibroblasts attached to synthetic scaffolds, Eur. J. Oral. Sci., 1999, pp. 282-289.
Ortiz-Urda, et al. Injection of genetically engineered fibroblasts corrects regenerated human epidermolysis bullosa skin tissue, The Journal of Clinical Investigation, 2003, pp. 251-255.
Suthin, et al. Enhanced expression of vascular endothelial growth factor by periodontal pathogens in gingival fibroblasts, J. Periodont. Res., 2003, pp. 90-96.
Mackenzie, et al. Keratinocyte Growth Factor Expression in Human Gingival Fibroblasts and Stimulation of In Vitro Gene Expression by Retinoic Acid, J. Periodontol., 2001, pp. 445-453.
International Search Report for PCT/JP2007/074962 conducted on Feb. 18, 2008.

* cited by examiner

*Primary Examiner* — Ruth Davis
(74) *Attorney, Agent, or Firm* — Turocy & Watson, LLP (57) ABSTRACT

A material for ameliorating skin tissue provided by the invention comprises, as a main component, a culture obtained by culturing cells or tissue fragments derived from human or other mammalian alveolar mucosa. Typically, 50% or more of the cells contained in the culture are fibroblasts, and having a high growth rate and a high productivity in vascular endothelial cell growth factor (VEDF) and/or keratinocyte growth factor (KGF).

4 Claims, 5 Drawing Sheets

MATERIAL FOR AMELIORATING SKIN TISSUE AND METHOD FOR PRODUCING THE SAME

CROSS-REFERENCE TO RELATED APPLICATIONS

This application is a Continuation of PCT International Application Serial No. PCT/JP2007/074962 filed Dec. 26, 2007.

This application is based upon and claims priority from Japanese Patent Application No. 2006-354259, filed Dec. 28, 2006, the entire contents of which are incorporated herein by reference.

TECHNICAL FIELD

The present invention relates to the use of cells from specific sites in the oral cavity, more specifically to a skin tissue ameliorating material (skin tissue ameliorating composition) which is based on such cells, and to a method for producing the same. The invention also relates to a method of ameliorating skin tissue using cells derived from oral tissue.

BACKGROUND ART

Various types of biomaterials are used as skin tissue restoring materials to repair skin tissue abnormalities or loss due to trauma or disease, and deformation such as congenital or acquired (age-associated) wrinkles and depressions.

For example, Patent Document 1 discloses a method in which dermal fibroblasts isolated from the skin tissue of the patient himself or herself are cultured in vitro, following which the culture is injected into skin tissue (affected site). Non-Patent Document 1 describes a method in which bovine collagen (atelocollagen) from which the C-terminal and N-terminal peptide portions have been removed to lower the antigenicity is injected at the affected site. Non-Patent Document 2 describes a method in which a hyaluronic acid gel is injected at the affected site. Non-Patent Document 3 describes a structure for implantation which is composed of pulpal fibroblasts or gingival fibroblasts adsorbed onto a substrate made of polyglycolic acid.

Patent Document 1: International Publication No. WO 97/04720
Non-Patent Document 1: DeLustro, F., et al.: J. Biomed Mater. Res. 20(1), pp. 109-120 (1986)
Non-Patent Document 2: Duranti, F., et al.: Dermatol. Surg. 24(12), pp. 1317-1325 (1998).
Non-Patent Document 3: Buurma, B., et al.: Eur. J. Oral Sci. 107, pp. 282-289 (1999).

However, because the biochemical materials (non-living tissue) described in each of the above-cited articles (Non-Patent Documents 1 to 3) are easily hydrolyzed in vivo and soon disappear from the site of administration, the advantageous effects do not persist. Also, when this type of material is used, it is difficult to completely eliminate immunological effects.

In a method like the one described in the above international publication (Patent Document 1) where dermal fibroblasts from the patient himself or herself are cultured in vitro, following which the culture is injected into skin tissue (affected site), although immunological effects do not arise, the cultured cells injected to the affected area do no more than function as a filler in the skin tissue (affected area) to be repaired. Such cells do not have a sufficient capability to actively improve the physiological state of skin tissue (physical state and/or nutritional state of skin tissue) at the affected site and in the surrounding region.

DISCLOSURE OF THE INVENTION

Accordingly, the present invention creates a biocompatible material which differs in content from conventional skin tissue restoring materials (i.e., affected area fillers), the object of the invention being to provide a skin tissue ameliorating material (i.e., a skin tissue ameliorating material which contains live cells) that has the ability to restore (fill) skin tissue (affected areas) where abnormalities or defects have occurred and is also capable of improving the physiological state of skin tissue at the affected area and its periphery to a healthier state. A further object of the invention is to provide a method which is capable of suitably manufacturing such a skin tissue ameliorating material. A still further object of the invention is to provide a method for using such a skin tissue ameliorating material; that is, a method for applying the material to an affected site (skin tissue) and ameliorating the physiological state of the affected area.

The skin tissue ameliorating material (i.e., composition for ameliorating skin tissue) provided by this invention is characterized by comprising, as a main component, a culture (which includes cultured cells; the same applies below) obtained by culturing cells or a tissue fragment derived from human or other mammalian alveolar mucosa. Typically, the skin tissue ameliorating material provided by this invention includes the culture and a pharmaceutically acceptable medium.

In the present specification, "skin tissue" is a term which, except where particular mention is made, should be broadly interpreted, and is a term which encompasses epidermal, dermal and subcutaneous tissue.

Figure 1:
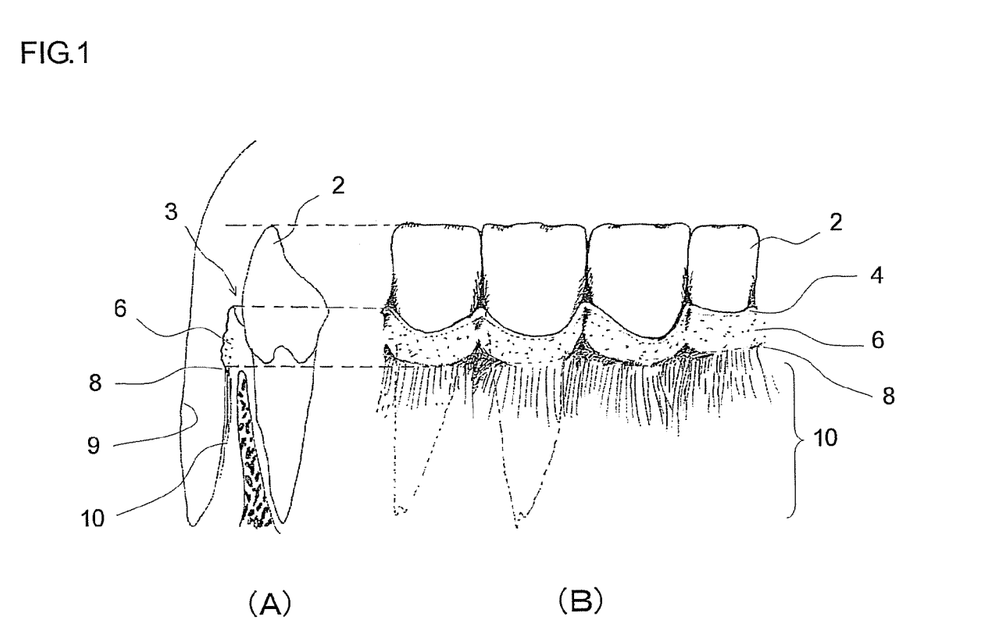
FIG. 1 schematically shows where the alveolar mucosa is located in the oral cavity.
Figure 2:
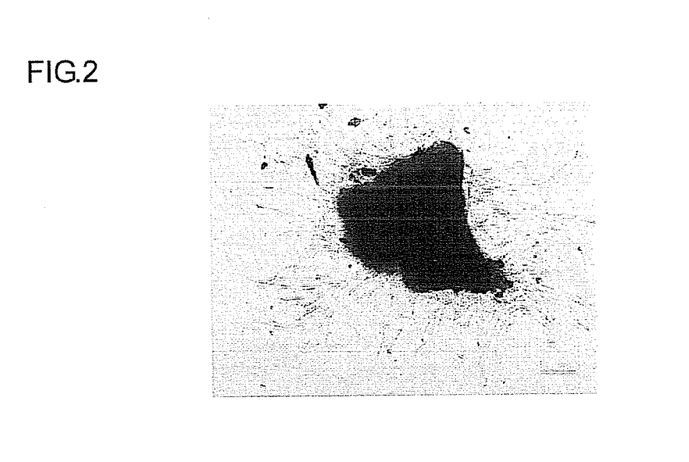
FIG. 2 is a micrograph showing the state of an alveolar mucosa-derived culture (cultured cells and tissue fragment) on day 7 following the start of culturing in a test example.
Figure 3:
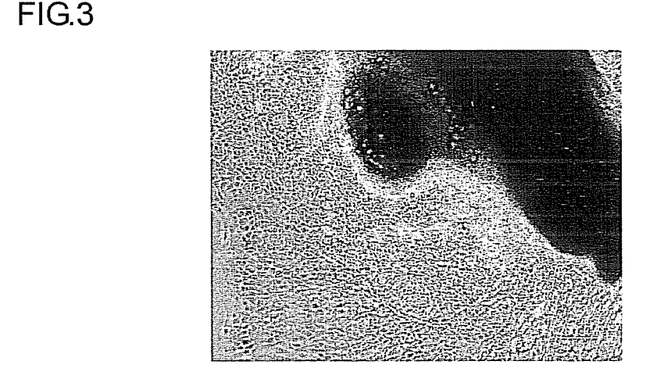
FIG. 3 is a micrograph showing the state of a palate-derived culture (cultured cells and tissue fragment) on day 7 following the start of culturing in a test example.
Figure 4:
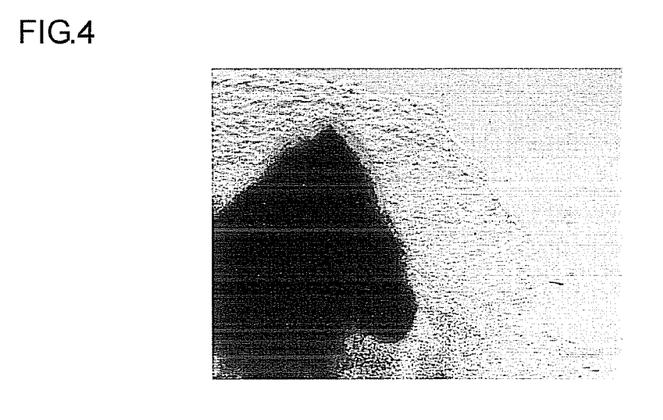
FIG. 4 is a micrograph showing the state of an attached gingival-derived culture (cultured cells and tissue fragment) on day 7 following the start of culturing in a test example.
Figure 5:
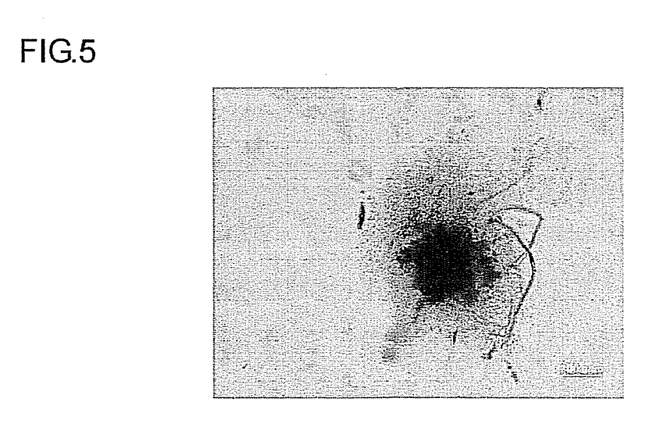
FIG. 5 is a micrograph showing the state of a buccal mucosa-derived culture (cultured cells and tissue fragment) on day 7 following the start of culturing in a test example.

In this specification, "alveolar mucosa" is a term which indicates a specific area within the oral cavity, and the meaning of which is generally understood in the field of dentistry or oral surgery. As carefully depicted in FIGS. 1A and 1B showing a lower premolar 2 and tissue in and around the cheek, the alveolar mucosa 10 is tissue having movable portions which move from the mucogingival junction 8 to the buccal mucosa 9 and the floor of the oral cavity (not shown), and lines the alveolar bone. The interval from the alveolar mucosa 10 to the lip (not shown) is the oral vestibule. The alveolar mucosa 10 lacks the keratinized layer seen in the gums. Also shown in the diagram are the gingival sulcus 3, the peripheral gingiva (free gingiva) 4, and the attached gingiva (non-movable gingiva) 6. These sites and the alveolar mucosa 10 are clearly distinguishable within the oral cavity. Of course, similar alveolar mucosa are present not only in the regions shown in FIGS. 1A and 1B, but also in the vicinity of the incisors.

The inventors have discovered that, in applications for ameliorating (which includes repairing) skin tissue, when cells (typically a mass composed of numerous cells, i.e., a cell mass) or a tissue fragment collected from alveolar mucosa within the oral cavity at a site differing from the skin tissue in question (the affected area) are cultured, and the resulting culture, which is a suspension of cultured cells, were administered to the affected site (skin tissue), not only a filling effect in the skin tissue, but marked improvements in the physiological state at the site of administration and at surrounding sites (e.g., acceleration of cell division in the epidermis, improvements in the physical state such as skin color, luster, fullness and texture, and/or improvements in the nutritional status of the skin) can also be observed. This discovery ultimately led to the present invention.

That is, in the skin tissue ameliorating material described herein, cell types (typically fibroblasts derived from alveolar mucosa) capable of exhibiting good skin tissue ameliorating effects either are present in a high proportion, or can be grown in a high ratio, within a culture derived from alveolar mucosa (primarily cultured cells) of which the material is primarily made. Therefore, when various cell growth factors (e.g., VEGF, KGF) are continuously produced at an affected area (i.e., supplied to an affected area) by means of the skin tissue ameliorating material described herein, addition to exhibiting a filling effect at sites of skin tissue (typically, subcutaneous tissue) deformation or loss similar to that of conventional skin tissue restorative materials, the physiological state at the affected area and in surrounding skin tissue can be improved.

One preferred embodiment of the skin tissue ameliorating material described herein is characterized in that at least 50% of the cells contained in the culture are fibroblasts. Fibroblasts from alveolar mucosa are active producers of the group of cell growth factors (VEGF, KGF, etc.), and have a good collagen (e.g., type I collagen, type III collagen) producing ability. As a result, in addition to a skin tissue restoring (filling) effect, a high skin tissue ameliorating effect can be obtained. Therefore, by including a high ratio of fibroblasts from alveolar mucosa, the skin tissue ameliorating effect can be further increased.

In addition, it has become apparent from the results of a comprehensive analysis of gene expression that fibroblasts derived from alveolar mucosa have a higher expression efficiency for antioxidant enzyme-related genes (e.g., superoxide dismutase 2 (SOD2), superoxide dismutase 3 (SOD3), superoxide dismutase 1 (SOD1)) which are thought to participate in anti-aging than do fibroblasts obtained from other sites (e.g., the dermal portion of the skin). Therefore, by applying a skin tissue ameliorating material containing a high concentration of fibroblasts from alveolar mucosa, anti-aging effects can be imparted to the affected site and surrounding skin tissue.

Another preferred embodiment of the skin tissue ameliorating material described herein is a skin tissue ameliorating material prepared in the form of a suspension containing cultured cells obtained by culturing, in vitro, cells or a tissue fragment derived from the aforementioned alveolar mucosa. Rapid amelioration of skin tissue can be achieved by the administration (injection to the affected site) of a cell suspension containing a high concentration of growth factor.

For example, a skin tissue ameliorating material which is essentially composed of a suspension having a vascular endothelial growth factor (VEGF) content of at least 30 pg per milliliter of protein in the suspension supernatant is especially preferred, and/or a skin tissue ameliorating material which is essentially composed of a suspension having a keratinocyte growth factor (KGF) content of at least 0.5 ng per milliliter of protein in the suspension supernatant is especially preferred. Rapid improvement in the skin tissue can be achieved by administering (injecting to the affected site) a cell suspension containing these growth factors in a high concentration, and more preferably by administering (injecting to the affected site) a cell suspension containing fibroblasts from alveolar mucosa which are capable, as mentioned above, of producing a high ratio of antioxidant enzyme.

Therefore, the present invention, according to another aspect, provides a method of supplying VEGF and/or KGF to skin tissue (affected area), which method is characterized by administering fibroblasts from alveolar mucosa (preferably in the form of a cell suspension) to the affected area. It also provides a method of supplying an antioxidant enzyme (e.g., the above-mentioned SOD group) to the skin tissue (the affected area), which method is characterized by administering fibroblasts from alveolar mucosa (preferably in the form of a cell suspension) to the affected area. In addition, it also provides a method of producing VEGF and/or KGF and a method of producing antioxidant enzyme (e.g., the above-mentioned SOD group), which method is characterized by culturing, in vitro, cells from alveolar mucosa (typically fibroblasts).

The present invention also provides a preferred method for manufacturing the skin tissue ameliorating material described herein. That is, the inventive method of manufacturing includes the steps of providing cells (typically a cell mass) or a tissue fragment derived from human or other mammalian alveolar mucosa, culturing the cells or tissue fragment derived from alveolar mucosa to obtain, and recovering the culture (primarily cultured cells).

Preferably, the culture (cultured cells) are suspended in a suitable liquid medium. Also, it is preferable to prepare a suspension containing the cultured cells so as not to include substances which could become immunogens in the subject (patient) in which the skin tissue ameliorating material will be employed. In addition, it is preferable for the cells or tissue fragment derived from the alveolar mucosa to be provided for culturing be collected from the very subject (patient) who is the intended target of use, or from someone who is related by blood.

With the method described herein, cells (typically fibroblasts) suitable for the intended purpose can be grown by culturing the acquired cells or a tissue fragment derived from the alveolar mucosa of the oral cavity, enabling a skin tissue ameliorating material which exhibits the above-described advantageous effects to be efficiently manufactured.

In a preferred embodiment of the method for manufacturing a skin tissue ameliorating material described herein, a culture characterized in that at least 50% of the cells contained in the culture are fibroblasts is recovered. By recovering such a culture, a preferred skin tissue ameliorating material which contains a high ratio of fibroblasts from alveolar mucosa can be provided. The fibroblasts from alveolar mucosa have a relatively high growth rate (compared with, for example, dermal skin cells) during in vitro cultivation, making it possible to efficiently produce the desired amount of fibroblasts in a short period of time. For this reason, restorative treatment and ameliorating treatment of skin tissue (affected site) can be rapidly carried out.

In another preferred embodiment of the skin tissue ameliorating material described herein, cells or a tissue fragment derived from the alveolar mucosa are placed in a given culture vessel (e.g., a cell culture dish or flask) and culturing is started. Once a confluent state (typically a state where the sidewalls on which growth is possible within the culture vessel are fully buried with cells that have grown) has been reached, culturing is continued for at least another two days (preferably at least four days), following which the culture (primarily cultured cells) is recovered.

By carrying out extended growth even after such a confluent state has been reached, it is possible to provide a skin tissue ameliorating material (e.g., an ameliorating material in the state of a cell suspension) in a preferred state which contains a high concentration of growth factors such as those mentioned above.

In a preferred embodiment according to another aspect of the invention, growth is continued until the cells as a whole within the culture have a vascular endothelial growth factor (VEGF) expression level, at least at the mRNA level, which is at least more than twice the level of expression immediately after culturing is started, following which the culture (primarily cultured cells) is recovered. Alternatively, growth is continued until the cells as a whole within the culture have a keratinocyte growth factor (KGF) expression level, at least at the mRNA level, which is at least more than twice the level of expression immediately after culturing is started, following which the culture (primarily cultured cells) is recovered.

By carrying out extended growth using the level of expression at the mRNA level (typically carrying out extended growth for at least two days after a confluent state has been reached) as an indicator, a skin tissue ameliorating material (e.g., ameliorating material in the state of a cell suspension) of a preferred nature which contains a high concentration of these growth factors can be provided.

According to another aspect, the invention provides a method of restoring (or ameliorating) skin tissue at an affected area by injecting the skin tissue ameliorating material described herein to the affected area.

This method typically includes the steps of providing one of the skin tissue ameliorating materials (e.g., cells of a culture containing fibroblasts from human or other mammalian alveolar mucosa) described herein, and administering (implanting) the provided skin tissue ameliorating material (or the aforementioned cultured cells) to an affected area (skin tissue, e.g., subcutaneous tissue) in a subject.

Preferably, alveolar mucosal cells or a tissue fragment collected in advance from the subject are cultured in vitro, and the resulting culture (typically a cell suspension containing the cultured cells and a pharmaceutically acceptable medium (solvent)) are administered (injected) to an affected area (skin tissue, e.g., subcutaneous tissue) in the subject. By one of the methods described herein, it is possible to achieve rapid restoration and amelioration (e.g., anti-aging) of the skin tissue that is the affected area.

BRIEF DESCRIPTION OF THE DRAWINGS

FIG. 1A is a sectional view, and FIG. 1B is a front view.

BEST MODE FOR CARRYING OUT THE INVENTION

Preferred embodiments of the invention are described below. Matters other than those specifically discussed in the present specification (e.g., the contents of the skin tissue ameliorating material) which are essential for the implementation of this invention (e.g., general matters relating to methods of culturing and purifying cells, and the preparation of cell-containing biological drug composition) are matters of design variation that could be apprehended by individuals skilled in the art based on prior art in fields such as medicine, pharmacology, biochemistry, organic chemistry, protein engineering, molecular biology, veterinary medicine and hygienics. The present invention may be implemented based on the contents described in this specification and technical knowledge in these fields.

The entire contents of all documents cited in this specification are incorporated herein by reference.

The skin tissue ameliorating material described herein may be a skin tissue ameliorating material (pharmaceutical composition) for humans or other mammals, and is a skin tissue ameliorating material consisting primarily of cells from human or other mammalian alveolar mucosa (typically fibroblasts from alveolar mucosa).

To the extent that the culture (primarily cultured cells) derived from the alveolar mucosa is capable of producing various cell growth factors and/or substances (typically, antioxidant enzymes) thought to participate in anti-aging which are suitable for the objects of the present invention, no particular limitation is imposed on the type of cell present in the culture or on the cell density, although it is preferable for the above reasons that the ratio of fibroblasts be high. For example, of all the cells present in the culture, it is preferable for at least 50%, and more preferable for at least 70%, to be fibroblasts. Fibroblasts from alveolar mucosa have a high growth rate when cultured in vitro, and have the ability to efficiently produce various cell growth factors (typically VEGF or KGF).

Generally, because of immunological problems, it is preferable to use as a component of the inventive material a culture (cultured cells) from alveolar mucosa (typically collected as a cell mass or tissue fragment) obtained from a mammal of the same species as the target of administration (subject), and it is especially preferable to use a culture derived from alveolar mucosa collected beforehand from the target of administration (patient) (autologous cultured cells).

In cases where a cell culture (cultured cells) is used as the primary component of the skin tissue ameliorating material, owing to the repeated subculturing of cultured cells at the stage of actual use, the appearance and other qualities of the cells may differ from the primary cells collected from alveolar mucosa. As used herein, "alveolar mucosal cells" encompasses cells after such subculturing.

The method of collecting alveolar mucosal cells or a tissue fragment may be similar to conventional methods for collecting this type of cell or tissue fragment; special treatment is not required. For example, a portion of the alveolar mucosa may be collected with techniques similar to various biopsies. For example, the desired alveolar mucosal cells (cell mass) or tissue fragment may be obtained by punch biopsy or needle biopsy. Because the cells used in the practice of the invention may be collected from alveolar mucosa in the oral cavity, one advantage for the subject (or donor) is that any sampling scar will not be visible from the exterior.

The collected cells (cell mass) or tissue fragment may be cultured and grown by a method similar to conventional methods for culturing this type of cell, to establish a cell line. Preferred examples of culture media that may be used include common α-MEM media to which a suitable serum material, antibiotic or the like has been added, Eagle's medium, Dulbecco's modified Eagle's medium (DMEM medium) or the like. The cells are cultured within a suitable culture vessel at about 37° C. (preferably in a $CO_2$ incubator) until they reach a confluent state, and culturing is preferably continued for another several days (typically at least 2 days; preferably at least 4 days, such as from about 4 to about 12 days; and most preferably for at least 8 days, such as from 8 to 12 days). By continuously culturing for such a long time after a confluent state has been achieved, a culture (cultured cells) capable of very efficiently producing a cell growth factor (typically VEGF or KGF) can be prepared.

Moreover, if necessary, the cells can be repeatedly subcultured. The number of passages, while not subject to any particular limitation, is typically not more than 10 (e.g., from 3 to 6).

The suitable period for continuing the culture after the above-described confluent state has been achieved can be determined using preferably the VEGF and/or KGF expression level as the indicator. For example, by investigating the mRNA expression level in the culture (cultured cells), the level of expression of VEGF and/or KGF (or other growth factors) by the cultured cells (typically fibroblasts) which make up the culture can be investigated and a suitable period for continuing the culture can be determined. Alternatively, it is possible to determine a suitable period for continuing the culture by investigating the level of expression by genes related to antioxidant enzymes such as the SOD group (e.g., SOD1, SOD2, SOD3).

Various conventional known techniques (e.g., real-time PCR analysis, Northern blot analysis) may be used to measure the mRNA expression level. The technique used for this purpose is not a distinctive feature of the invention, and so a detailed explanation is omitted here.

After the desired amount of cultured cells has been produced by culturing as described above, the culture containing the target cells is recovered from the culture vessel. The method of recovery may be similar to ones used in conventional cell culturing; special operations and treatment are not required to implement the present invention. For example, the cells which have attached to the inside wall of the culture vessel (typically a dish or flask) are freed by treatment with a suitable enzyme (e.g., trypsin) and recovered together with the liquid culture. Next, the recovered cells are cultured for preferably at least 12 hours, and more preferably at least 24 hours, in a suitable serum-free culture medium. In this way, immunogenic substances (typically serum ingredients) present in the medium can be substantially removed. Moreover, the cultured cells can be frozen and preserved by a conventional known method.

The cell suspension (i.e., a composition containing, as the primary ingredients, cultured cells, a suitable serum-free medium, a suitable buffer and a suitable solvent) from which immunogenic substances have been substantially removed in this way may serve as a skin tissue ameliorating material according to the invention.

Aside from the cell culture and a pharmaceutically acceptable medium (typically a culture medium such as serum-free medium, or a solvent such as a buffer solution) being the main components, the skin tissue ameliorating material may include various types of accessory ingredients. Examples of preferred accessory ingredients include (1) antibiotics, (2) various vitamins, glucose and other nutrients, (3) enzymes, (4) coenzymes, (5) preservatives, (6) growth factors such as KGF and VEGF, and other cytokines, (7) various drugs (e.g., anti-inflammatories), and (8) colorants.

The skin tissue ameliorating material that has been prepared may be administered to the same affected areas like conventional skin tissue ameliorating materials (see, for example, the above-cited International Publication No. WO 97/04720 and journal articles (the document by F. DeLustro et al. and the document by F. Duranti et al.)). The entire content of these cited documents is incorporated in this specification by reference.

Typically, a skin tissue ameliorating material in the form of a cell suspension can be injected to the subcutaneous tissue using a suitable syringe or the like. The skin tissue ameliorating material is not limited to the form of a suspension, and may also be used in the form of a mass of cultured cells (e.g., a mass formed of cells that have gathered together into the form of a sheet). In such cases, administration is typically carried out as a composite of the cell culture and a matrix. Various types of suitable biocompatible materials (e.g., organic polymeric materials such as polysaccharides and proteins, and inorganic materials) may be used as the matrix. Typical examples of preferred matrixes include human blood (preferably from the subject himself or herself), or plasma materials of various contents such as platelet-rich plasma (PRP). Artificial matrixes composed of alginic acid, collagen or the like may also be used.

The dose and number of administrations (and dosing interval) of the prepared skin tissue ameliorating material may vary depending on the symptoms, and thus are not subject to any particular limitation. These are generally matters to be decided by the physician and other caregivers, and thus do not limit the present invention.

The skin tissue ameliorating material described herein may also be employed for ameliorating tissue within the oral cavity, particularly gingival tissue. That is, the present invention, according to another aspect, provides an oral tissue ameliorating material, particularly a gingival tissue ameliorating material, which comprises, as a main component, a culture obtained by culturing cells or a tissue fragment derived from human or other mammalian alveolar mucosa.

Several examples relating to the present invention are described below, although these examples are not intended to limit the invention.

Test Example 1

Alveolar mucosa from two adult subjects (referred to below as Subject A and Subject B) were collected at the Oral and Maxillofacial Department at Nagoya University Hospital. Specifically, using a 3 mm diameter punch biopsy, a portion of the alveolar mucosa (tissue fragment) was collected from two random places. The tissue fragments had a diameter of about 3 mm and a thickness of about 2 mm. For comparison, tissue fragments of the same shape were similarly collected by punch biopsy from the palate, the attached gingiva (see FIG. 1), and the buccal mucosa in the same subjects.

The tissue fragments thus obtained were disinfected by one minute of immersion in 12% Isodine (registered trademark) solution. Next, each tissue fragment was cut into four equal portions with a scalpel, immersed in a collagenase solution (product of Wako Pure Chemical Industries, Ltd.; collagenase concentration, 10 mg/mL), and collagenase treatment was carried out at 37° C. for 1 hour, thereby disaggregating the tissue.

The tissue that was disaggregated into bits by the above treatment was cultured in a culture vessel (number of tests n=4). Specifically, the tissue suspension following the above collagenase treatment was dispensed with a pipette to each well of a commercial 6-well culture plate (culture surface area, about 9.2 cm$^2$), 3 mL of DMEM medium (Sigma-Aldrich product No. D6429) containing 10% fetal bovine serum (FBS; Invitrogen product No. 10099-141) was added, and culturing was started under the conditions of 37° C. and 5% $CO_2$.

Next, a suitable amount (about 1 mL) of the culture supernatant was collected when 2 days, 4 days, 7 days, 9 days, 11 days, 14 days, 16 days and 18 days had elapsed following the start of culturing, and the concentration of soluble collagen was measured with a commercial soluble collagen assay kit (Sircol Collagen Assay Kit; a product of Funakoshi KK). When culture supernatant was collected, the well was successively replenished with fresh DMEM medium in an amount corresponding to the sampled amount.

The state of cell growth at the bottom of each plate was examined using an inverted microscope (magnification: 100×) when 4 days, 7 days and 16 days had elapsed following the start of culturing.

Also, when 14 days had elapsed following the start of culturing, the ratio of the surface area occupied by the cultured cells relative to the total culture surface area at the bottom of the plate (total cell occupancy, %) was determined. More specifically, the cultured cells distributed at the bottom of the plate were demarcated into fibroblasts and keratinocytes based on outer shape. The fibroblast occupancy (%) and the keratinocyte occupancy (%) were then determined, based on a value of 100% for the total culture surface area at the bottom of the plate.

When 16 days had elapsed from the start of culturing, it was confirmed that a confluent state had already been achieved, but culturing was continued further under the same conditions. Then, 22 days after the start of culturing, the medium (supernatant) was discarded from the wells to which tissue fragments still adhered and the wells were washed with PBS, after which a 0.05% trypsin-EDTA solution was added, thereby immersing the culture adhering to the bottom of the wells in the solution. Then, with 10 minutes of standing at 37° C., the culture (cultured cells) was freed from the sidewalls of the well by such trypsin treatment and recovered. The number of recovered cells was subsequently counted using a cell counting and analysis system (a product available from Scharfe System under the registered trademark CASY). The results of each of the above tests are shown below.

The amount of collagen produced by cultured cells from four types of tissue fragments (alveolar mucosa, palate, attached gingival, buccal mucosa) was investigated using the above-described soluble collagen measurement kit; a difference in the amount of collagen produced was not observed among the collected tissue fragments. Test samples from 2 days to 14 days after the start of culturing each had soluble collagen concentrations of from about 130 to 150 μg/mL. In test samples from 16 days to 18 days after the start of culturing (that is, after a confluent state had been reached), the soluble collagen concentration was about 160 to 180 μg/mL.

The state of cell growth at the bottom of each plate was examined using an inverted microscope (magnification: 100×) when 4 days, 7 days and 16 days had elapsed following the start of culturing. Compared with cultures from three types of tissue fragments (palate, attached gingival, buccal mucosa), the culture from the alveolar mucosa had a particular high abundance of fibroblasts, indicating that the growth rate was also rapid. FIGS. 2 to 5 are micrographs showing the state of cultures on day 7 of culturing for each type of tissue fragment collected from Subject A (the scale bar in the images is 200 μm). As is apparent from these micrographs, in the culture derived from alveolar mucosa shown in FIG. 2, fibroblasts were being observed to have radially multiplied in the periphery of the tissue fragment. In the culture derived from the palate shown in FIG. 3 and in the culture derived from attached gingival shown in FIG. 4, fibroblasts were being observed in the periphery of the tissue fragment, but the proportion of such cells was found to be relatively low. In the culture derived from buccal mucosa shown in FIG. 5, epidermal cells (keratinocytes) were being observed to gather in the periphery of the tissue fragment, and the proportion of fibroblasts was found to be very low.

Figure 6:
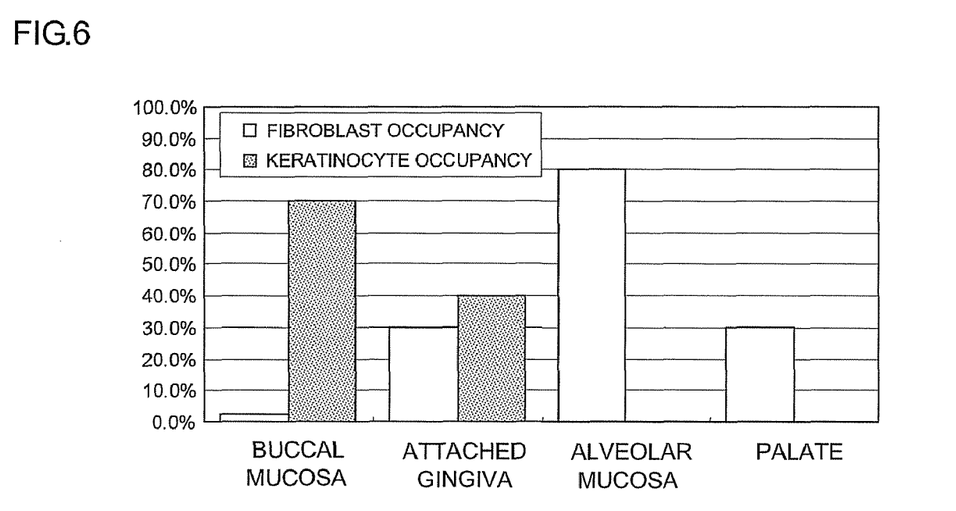
FIG. 6 is a graph showing the fibroblast occupancy (%) and keratinocyte occupancy (%) in the respective cultures related to one test example.
Figure 7:
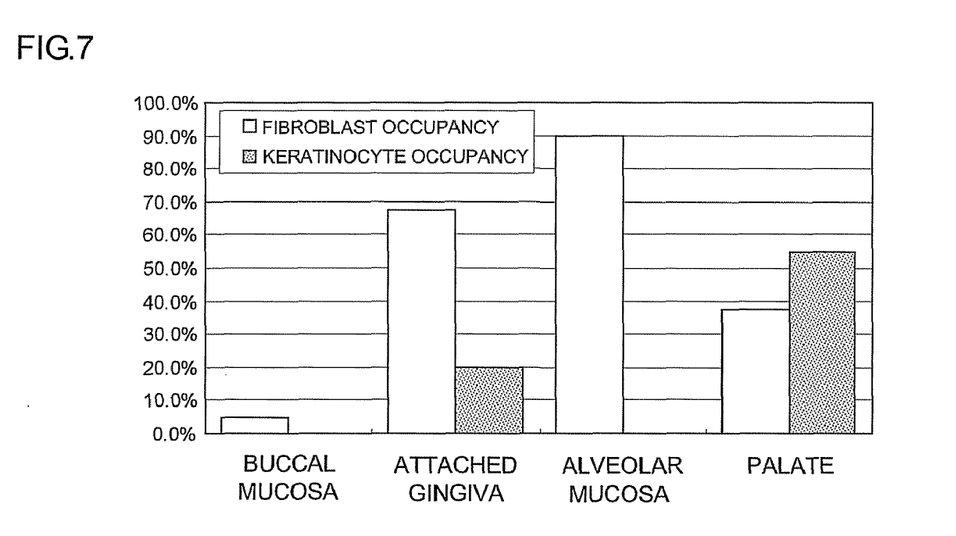
FIG. 7 is a graph showing the fibroblast occupancy (%) and keratinocyte occupancy (%) in the respective cultures related to another test example.

Graphs indicating the fibroblast occupancy (%) and keratinocyte occupancy (%) determined as described above after 14 days had elapsed from the start of culturing are shown in FIG. 6 for samples (tissue fragments) collected from Subject A, and are shown in FIG. 7 for samples (tissue fragments) collected from Subject B. As is apparent from the results shown in these graphs, in cultures derived from the alveolar mucosa, cell proliferation was good and most of the cells were fibroblasts. On the other hand, in cultures derived from the palate and cultures derived from the attached gingiva, the proportion of fibroblasts was found to be low and the proportion of keratinocytes (epidermal cells) was found to be high. And in cultures derived from buccal mucosa, the presence of fibroblasts was very low, with most of the multiplied cells being keratinocytes (epidermal cells).

Figure 8:
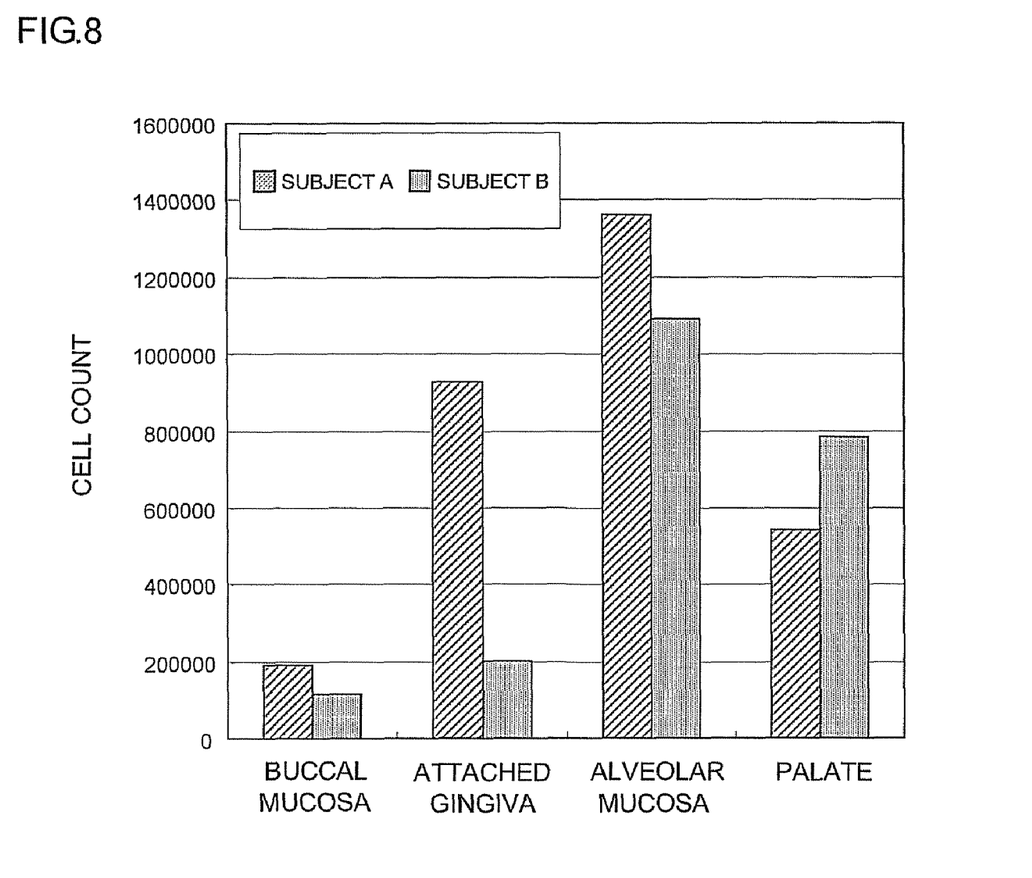
FIG. 8 is a graph showing the number of cells in each culture related to the test examples.

Also, FIG. 8 shows the number of cells counted with the above-mentioned cell counting and analyzing system following trypsin treatment and recovery 22 days after the start of culturing (when culturing had been carried out for about another 6 days after a confluent state had been reached). As is apparent from the results shown in this graph, regardless of whether the samples were collected from Subject A or Subject B, the cell count was highest for cultures derived from alveolar mucosa, indicating a good ability to multiply.

As is apparent from the above results, by culturing, among the diverse tissues in the oral cavity, a cell mass or tissue fragment collected from particularly the alveolar mucosa, it is possible to obtain a culture (cultured cells) having a high proportion of fibroblasts and a high growth efficiency; that is, a skin tissue ameliorating material.

Test Example 2

Alveolar mucosa (in two subjects) and a portion of the dermis from behind the ear (in two subjects) was collected from a plurality of adult subjects (a total of four persons) at the Oral and Maxillofacial Department at Nagoya University Hospital. Specifically, using a 3 mm diameter punch biopsy, portions of the alveolar mucosa (tissue fragment) or portions of the earlobe dermis were collected from two random places. The tissue fragments thus obtained were disinfected by one minute of immersion in 12% Isodine (registered trademark) solution. Next, each tissue fragment was cut into four equal portions with a scalpel, immersed in a collagenase solution (product of Wako Pure Chemical Industries, Ltd.; collagenase concentration, 10 mg/mL), and collagenase treatment was carried out at 37° C. for 1 hour, thereby disaggregating the tissue.

The tissue that was disaggregated into bits by the above treatment was cultured in a culture vessel. Specifically, the tissue suspension following the above collagenase treatment was dispensed with a pipette to a plurality of wells in a commercial 6-well culture plate (culture surface area, about 9.2 cm$^2$), 3 mL of DMEM medium (containing 10% FBS) was added, and culturing was started under the conditions of 37° C. and 5% $CO_2$. A substantially confluent state was reached when 16 days had elapsed from the start of culturing, but culturing was continued further under the same conditions.

The cultures (cultured cells) in several of the wells were recovered by the above-described trypsin treatment on days 4, 8, 12, 16, 20 and 24 following the start of culturing. Next, the total RNA was extracted by a conventional method from the resulting cultures.

Total RNA samples from cultured cells of alveolar mucosa (abbreviated below as "alveolar mucosal RNA samples") and total RNA samples from cultured cells of earlobe dermal tissue (abbreviated below as "dermal tissue RNA samples") were obtained in this way for each of the above culture periods.

Next, using a general real-time PCR (RT-PCR) method on the resulting RNA samples as the materials, the VEGF and KGF expression levels were investigated by a relative determination method using the mRNA expression level as the indicator. Specifically, cDNA was prepared using reverse transcriptase from each of the RNA samples and, using the cDNA sample as the template, real-time PCR was carried out in accordance with the guide book provided by the manufacturer (Takara Bio). At this time, glyceraldehyde-3-phosphate dehydrogenase (GAPDH) was used as the reference gene (housekeeping gene). The VEGF primers and the KGF primers were real-time PCR primer sets (products) for exclusive use with the GeneChip (registered trademark) from (Affymetrix), and were procured from Takara Bio KK. The product information is given below.

Figure 9:
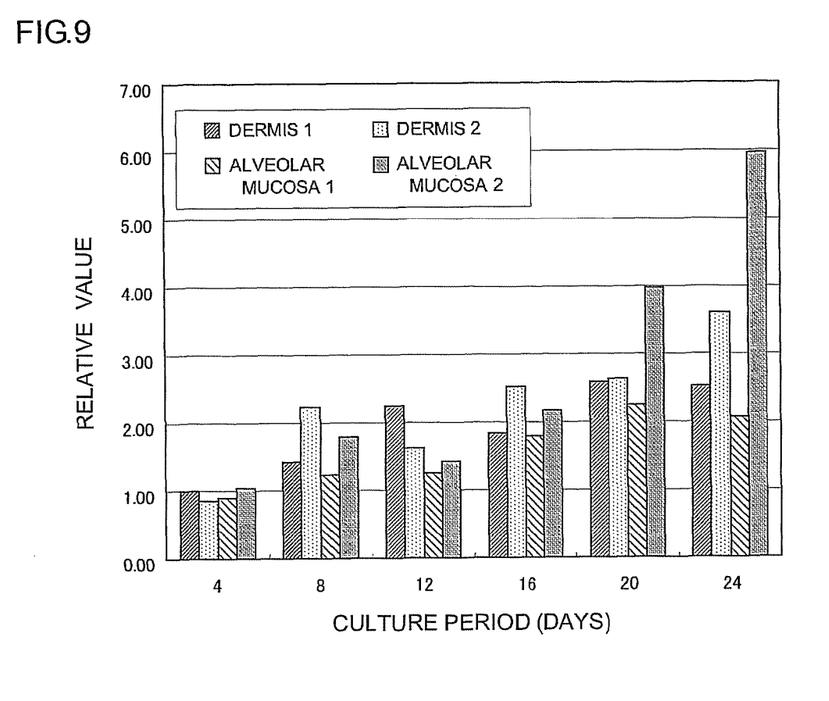
FIG. 9 is a graph showing relative values for vascular endothelial growth factor (VEGF) expression levels, with respect to the expression level at the mRNA level as the indicator, in each culture related to the test examples.

(1) VEGF: GenBank Acc: NM 001025366, Gene ID: HA074937; Description: *Homo sapiens* vascular endothelial growth factor (VEGF), transcript variant 1, mRNA
(2) KGF: GenBank Acc: NM 002009, Gene ID: HA035992; Description: *Homo sapiens* fibroblast growth factor 7, (keratinocyte growth factor) (KGF7), mRNA The results obtained by the above real time PCR are shown in FIG. 9 (VEGF) and FIG. 10 (KGF). In these graphs, VEGF and KGF are both indicated as relative values (no units) of the expression level, with respect to the VEGF mRNA expression level or the KGF mRNA expression level (represented as a value of 1) determined from a dermal tissue (collected from one subject)-derived RNA sample obtained from a culture on day 4 after the start of cultivation.

Figure 10:
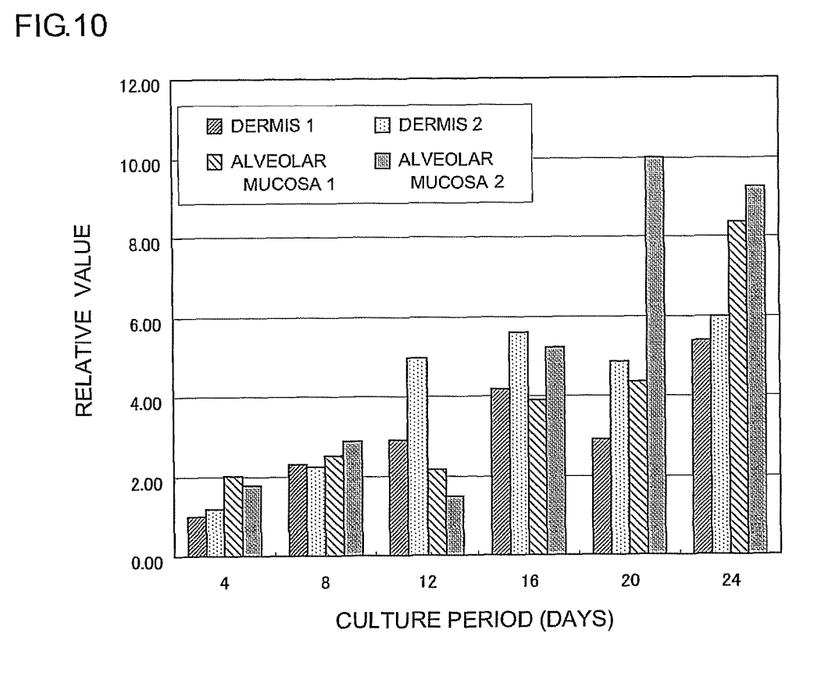
FIG. 10 is a graph showing relative values for keratinocyte growth factor (KGF) expression levels, with respect to the expression level at the mRNA level as the indicator, in each culture related to the test examples.

As is apparent from these graphs, the RNA samples from alveolar mucosa were found to have a VEGF expression level and a KGF expression level which were higher overall than RNA samples from dermal tissue. In particular, with continued culturing after a confluent state had been reached, the VEGF expression level and the KGF expression level rose sharply in cultures from alveolar mucosa. Cultures on day 20 and thereafter following the start of culturing were observed to have an expression level (the mRNA level) at least twice the expression level shortly after the start of culturing (e.g., up to day 4 after the start of culturing), and in good cases, an expression level (mRNA level) more than four times thereof shortly after the start of culturing. It was thus being verified from these test examples that recovering the culture after continuing cultivation further (preferably continuing it for at least 4 days) once a confluent state has been reached is preferable for manufacturing a skin tissue ameliorating material.

Test Example 3

Alveolar mucosa was collected from Subject A in the same way as in Test Example 1. The collected tissue fragment was subjected to 1 hour of collagenase (Wako Pure Chemical Industries, Ltd.; concentration, 10 mg/mL) treatment at 37° C. The resulting treated tissue fragments were transferred to a 3.5 cm diameter culturing dish containing DMEM culture medium, and cultured at 37° C. under 5% $CO_2$. Next, a T75 flask containing DMEM medium which includes 10% FBS and 1% antibiotic-antifungal agent (Invitrogen product No. 15240-062) was prepared, then the above-described culture from an alveolar mucosal tissue fragment was placed in the flask and cultured for 7 days at 37° C. and under 5% $CO_2$. The culture was then treated with a commercial cell dissociating agent (Invitrogen product; TrypLE Select (trade name)), and cultured cells (primarily fibroblasts) attached to the culture flask were freed and recovered. The number of recovered cells was counted using the above-mentioned cell counting and analyzing system.

Next, approximately $2\times10^7$ of these cells were dyed (fluorescent labeled) using a commercial fluorescent dye kit (product of Sigma-Aldrich; PKH26 Red Fluorescent Cell Linker Mini Kit). The fluorescent labeled cells were suspended using PBS, thereby providing a cell suspension (i.e., a skin tissue ameliorating material) according to these test examples. In addition, the cell concentration was adjusted to about $1\times10^7$ cells/mL, and thereafter the suspension was implanted into the dermis on a dorsal region of nude mice.

Two months later, the implanted tissue was collected, and the tissue was fixed using 4% formaldehyde solution (Sigma-Aldrich product) as the fixing solution. The fixed tissue was then embedded in Tissue-Tek O.C.T. Compound (Sakura Finetechnical product), and prepared as sections having a thickness of about 6 μm.

Next, using these sections and anti-human collagen type I monoclonal antibodies a (Chemicon product), immunostaining was carried out with an immunofluorescent antibody technique. Specimens were then prepared using a commercial mounting medium for immune tissue staining (Vectashield (registered trademark) Mounting Medium for Fluorescence with DAPI (a Vector Laboratories product), and the specimens were examined under a microscope.

As a result, after two months had elapsed, the cells (skin tissue ameliorating material) implanted in nude mice were ascertained to be in place (i.e., to be alive) within the dermis just as at the time of implantation. Moreover, human type I collagen was present in the implanted cellular cytoplasm and the periphery thereof. This demonstrated that cells from alveolar mucosa (primarily fibroblasts) produce type I collagen even after implantation.

Test Example 4

As in Test Example 3, samples of alveolar mucosa were collected and disinfected, then cut into smaller pieces and the epidermis separated, following which cell culturing was started. Culturing was then carried out continuously for about one month. When at least the target cell count had been reached, the above-described trypsin treatment was carried out, followed by recovery. The cells were then washed twice with physiological saline, after which they were suspended with fresh physiological saline, thereby preparing a cell suspension (skin tissue ameliorating material) according to this test example.

Next, about 600 to 2,000 µL of this cultured cell suspension (skin tissue ameliorating material) was subcutaneously injected into affected areas (wrinkled areas on the forehead, wrinkled areas below the bottom eyelid) of a subject with a 1 mL syringe and a 30 G needle. Amelioration of wrinkles (e.g., diminution of linear depressions, increase in luster) on the skin at the surface of the affected areas (sites of injection) was noted with the passage of time by observing the subsequent progress.

INDUSTRIAL APPLICABILITY

It is possible to employ the skin tissue ameliorating material described herein to restore skin tissue and improve its physiological state. Therefore, this material is useful as a material for dermatological treatment (including plastic surgery and cosmetic surgery).

The invention claimed is:

1. A method for manufacturing a skin tissue ameliorating material, comprising:
   providing cells or a tissue fragment derived from human or other mammalian alveolar mucosa;
   culturing the cells or tissue fragment derived from alveolar mucosa in a given culture vessel, wherein the culturing is continued for at least another two days after a confluent state has been reached;
   recovering the cultured cells attached to the culture vessel by trypsin treatment: and
   preparing a cell suspension containing the recovered cultured cells.

2. The method according to claim 1, wherein at least 50% of the recovered cells are fibroblasts.

3. The method according to claim 1, wherein the cultured cells attached to the culture vessel are recovered after continuing the culturing until the cells as a whole contained in the cell culture have a vascular endothelial growth factor (VEGF) expression level, at least at an mRNA level, at least more than twice the expression level immediately after the culturing started.

4. The method according to claim 3, wherein the cultured cells attached to the culture vessel are recovered after continuing the culturing until the cells as a whole contained in the cell culture have a keratinocyte growth factor (KGF) expression level, at least at an mRNA level, at least more than twice the expression level immediately after the culturing started.

* * * * *